United States Patent
Balasubramanian et al.

(10) Patent No.: US 11,839,665 B2
(45) Date of Patent: Dec. 12, 2023

(54) HIGH STRENGTH AND TRANSLUCENCY DENTAL CERAMIC MATERIALS, DEVICES, AND METHODS

(71) Applicant: James R. Glidewell Dental Ceramics, Inc., Newport Beach, CA (US)

(72) Inventors: Sreeram Balasubramanian, Irvine, CA (US); Tyler Arthur Gubb, Newport Beach, CA (US); Akash, Irvine, CA (US); Thomas C. Valenti, Rancho Santa Margarita, CA (US); Yan Yang, Irvine, CA (US); Kevin Michael Recor, Mission Viejo, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 241 days.

(21) Appl. No.: 16/707,153

(22) Filed: Dec. 9, 2019

(65) Prior Publication Data

US 2020/0107996 A1   Apr. 9, 2020

Related U.S. Application Data

(63) Continuation of application No. 15/900,945, filed on Feb. 21, 2018, now Pat. No. 10,532,008.

(Continued)

(51) Int. Cl.
*A61K 6/818*  (2020.01)
*C04B 35/488*  (2006.01)
*C04B 35/486*  (2006.01)

(52) U.S. Cl.
CPC .......... *A61K 6/818* (2020.01); *C04B 35/486* (2013.01); *C04B 35/4885* (2013.01); *C01P 2004/62* (2013.01); *C01P 2004/64* (2013.01); *C01P 2006/10* (2013.01); *C01P 2006/14* (2013.01); *C01P 2006/16* (2013.01); *C04B 2235/3224* (2013.01); *C04B 2235/3225* (2013.01); *C04B 2235/3241* (2013.01); *C04B 2235/3277* (2013.01); *C04B 2235/608* (2013.01);

(Continued)

(58) Field of Classification Search
CPC ..... A61K 6/818; A61K 6/822; C01P 2004/62; C01P 2004/64; C01P 2006/10; C01P 2006/14; C01P 2006/16
See application file for complete search history.

(56) References Cited

U.S. PATENT DOCUMENTS

| | | |
|---|---|---|
| 4,279,655 A | 7/1981 | Garvie et al. |
| 5,326,518 A | 7/1994 | Kimura et al. |

(Continued)

OTHER PUBLICATIONS

Origin Beyond Plus, Material Safety Data Sheet, revision Oct. 16, 2016, in 6 pages.

*Primary Examiner* — Hoa (Holly) Le
(74) *Attorney, Agent, or Firm* — Charles Fowler

(57) ABSTRACT

A zirconia ceramic material for use in dental applications is provided comprising an yttria-stabilized zirconia material comprising from 4.5 mol % to 5.1 mol % yttria. Optionally, the zirconia ceramic has a coloring agent that may comprise one or more metals selected from terbium (Tb), chromium (Cr), erbium (Er), and cobalt (Co), and further, may, optionally, comprise alumina, which if present may be in an amount from 0 wt % to 0.25 wt %. The zirconia ceramic materials exhibit both enhanced translucency and a flexural strength of at least 800 MPa when fully sintered.

9 Claims, 1 Drawing Sheet

Related U.S. Application Data

(60) Provisional application No. 62/462,176, filed on Feb. 22, 2017.

(52) U.S. Cl.
CPC ............... *C04B 2235/6027* (2013.01); *C04B 2235/6567* (2013.01); *C04B 2235/96* (2013.01); *C04B 2235/9653* (2013.01); *C04B 2235/9661* (2013.01)

(56) References Cited

U.S. PATENT DOCUMENTS

| | | | |
|---|---|---|---|
| 6,087,285 A | 7/2000 | Oomichi et al. | |
| 7,806,694 B2 | 10/2010 | Brodkin et al. | |
| 8,936,848 B2 | 1/2015 | Jung et al. | |
| 9,309,157 B2 | 4/2016 | Fujisaki et al. | |
| 9,737,383 B2 | 8/2017 | Fujisaki et al. | |
| 9,783,459 B2 | 10/2017 | Gottwik et al. | |
| 9,802,868 B2 | 10/2017 | Johannes et al. | |
| 10,004,668 B2 | 6/2018 | Brodkin et al. | |
| 10,532,008 B2 | 1/2020 | Balasubramanian et al. | |
| 2010/0003630 A1 | 1/2010 | Yamashita et al. | |
| 2011/0027742 A1 | 2/2011 | Fujisaki et al. | |
| 2012/0058883 A1 | 3/2012 | Yamashita et al. | |
| 2012/0277088 A1* | 11/2012 | Mathers | C04B 35/6263 977/773 |
| 2013/0313738 A1 | 11/2013 | Carden | |
| 2014/0227654 A1 | 8/2014 | Fujisaki et al. | |
| 2015/0238291 A1* | 8/2015 | Hauptmann | A61C 13/0006 428/64.1 |
| 2015/0297466 A1* | 10/2015 | Jahns | C04B 41/5031 428/312.8 |
| 2016/0038381 A1 | 2/2016 | Jahns | |
| 2016/0310245 A1 | 10/2016 | Fujisaki et al. | |
| 2017/0020639 A1* | 1/2017 | Jahns | A61C 8/0012 |
| 2018/0133112 A1 | 5/2018 | Brodkin et al. | |
| 2018/0235847 A1 | 8/2018 | Balasubramanian et al. | |

\* cited by examiner

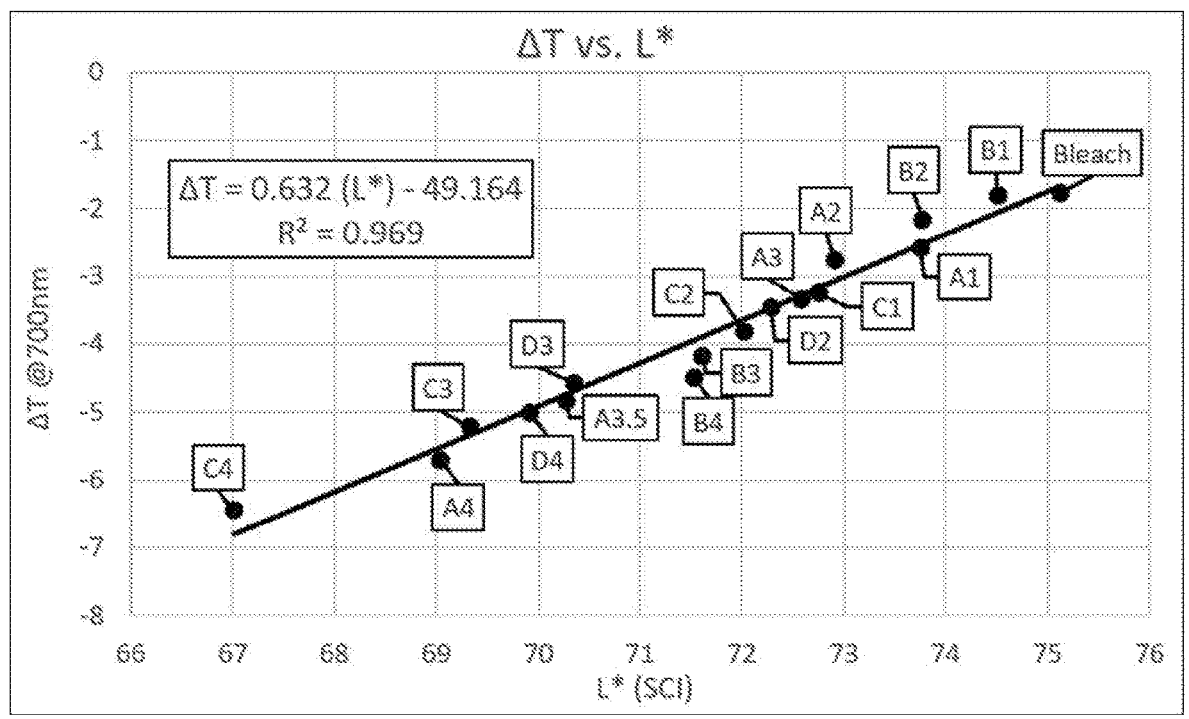

HIGH STRENGTH AND TRANSLUCENCY DENTAL CERAMIC MATERIALS, DEVICES, AND METHODS

This application is a continuation of, and claims the benefit of and priority to, U.S. patent application Ser. No. 15/900,945, filed Feb. 21, 2018, which claims the benefit of, and priority to, U.S. Provisional Patent Application No. 62/462,176, filed Feb. 22, 2017, which are all hereby incorporated herein by reference in their entireties.

BACKGROUND

Dental prosthetic devices—such as crowns, bridges, inlays, onlays, and veneers—are preferably formed from materials having good mechanical properties, including high flexural strength and high fracture toughness. In addition, these materials should preferably have good aesthetic characteristics, meaning that they have a natural appearance in color, texture, translucency, and shape so that they are not readily distinguishable from the original natural teeth.

Ceramic materials, and particularly yttria-stabilized zirconia (YSZ), have been widely adopted for use in dental restorations because these materials have high strength and high fracture toughness. For example, U.S. Pat. No. 9,309,157 (assigned to Tosoh Corporation) describes zirconia sintered bodies for use in dental applications that are formed from zirconia powder containing 2-4 mol % yttria as a stabilizer, and having reported three-point bending strength of 1,000 MPa or higher.

Conventional methods of manufacturing dental ceramic materials include molding a mixture of starting materials that includes yttria-stabilized zirconia powder into a green body, typically by press molding methods such as uniaxial pressing or cold isostatic pressing (CIP). In addition to the yttria-stabilized zirconia powder, the starting materials for the conventional press molding methods typically include a small amount (e.g., from 0-0.25 wt % of the zirconia powder) of aluminum oxide ($Al_2O_3$) as an additive, and an organic binder (e.g., from 0.5 to 10 wt %) to facilitate the press molding process. The green body can then be sintered at a sintering temperature of from 1350 to 1600° C. to obtain a zirconia sintered body.

Recent attention has been paid to increasing the concentration of yttria in zirconia powder starting materials used in dental ceramics in order to improve the translucency of the resulting sintered bodies. For example, US 2016/0310245 (also assigned to Tosoh Corporation) describes zirconia sintered bodies for use in dental applications that are formed from zirconia powder containing 4-6.5 mol % yttria as a stabilizer. The '245 publication describes sintered bodies having total light transmittance of 37-40% to light with a wavelength of 600 nm, however, the increased yttria concentration also has the result of decreasing the reported three-point bending strength to less than 900 MPa. In particular, in the examples having yttria concentrations of more than 4.1 mol % the sintered bodies had three-point bending strengths of less than 800 MPa.

The International Organization for Standardization (ISO) specification of requirements for ceramic materials used in dentistry—ISO 6872:2015—requires that materials used for monolithic ceramic prostheses of up to 3 units should have a flexural strength of at least 500 MPa. Additionally, ISO 6872:2015 requires that materials used for monolithic ceramic prostheses of 4 or more units should have a flexural strength of at least 800 MPa. Accordingly, it would be desirable to have dental ceramic materials and manufacturing methods that provide dental restorations having high translucency while still maintaining flexural strengths of greater than 500 MPa, or greater than 800 MPa.

SUMMARY

Methods for enhancing strength and translucency properties of sintered, zirconia ceramic bodies and zirconia ceramic dental restorations are provided. A method is provided for manufacturing a zirconia ceramic bisqued body having a high density and low porosity that is suitable for machining, milling, or other form of subtractive manufacturing to form a pre-sintered object, such as a pre-sintered dental restoration.

In a first aspect, a method of manufacturing a sintered ceramic body includes steps of making a ceramic green body using a wet forming process (e.g., slip-casting, filter pressing, centrifugal casting), bisque heating the green body to form a ceramic bisqued body, and sintering the bisqued body (or parts formed from the bisqued body) to obtain a ceramic sintered body. In a preferred embodiment, the wet forming process is a slip-casting process using zirconia as a starting material.

In a second aspect, a dental block device for producing a dental prosthesis includes an yttria-stabilized zirconia green body having a density between 56% to 60% theoretical density and having an yttrium oxide concentration between 4.7 mol % and 5.2 mol %. In an embodiment, the zirconia green body has a median particle size that is less than 350 nm, such as from 100 nm to 350 nm. In one embodiment the zirconia green body was made from a zirconia material having a median particle size that is less than 350 nm, such as from 100 nm to 350 nm.

In a third aspect, a dental block device for producing a dental prosthesis includes a zirconia bisqued body having a density of between 58% to 62% of theoretical density and having a porosity of between 38% and 42%, such as between 38% and 41%. In one embodiment, a bisque or pre-sintered body has a density increase of less than 3% relative to the density of the green body. In one embodiment, the peak temperature range for heating a green body to form a bisque body is between 900° C. and 1100° C. which is held between 0.25 hours and 24 hours. In an embodiment, the zirconia bisqued body includes yttrium oxide at a concentration between 4.7 mol % and 5.2 mol %. In another embodiment, the zirconia bisqued body has a median particle size that is less than 350 nm, such as from 100 nm to 350 nm. In another embodiment, the zirconia bisqued body is made from a zirconia material having a median particle size that is less than 350 nm, such as from 100 nm to 350 nm. In still another embodiment, the zirconia bisqued body includes a median pore diameter of less than 90 nm, such as from 35 nm to 90 nm.

In a fourth aspect, an unshaded zirconia sintered body includes a body containing yttria-stabilized zirconia having a flexural strength of at least 800 MPa, such as between 800 MPa and 900 MPa, and a total light transmittance value of at least 57%, such as between 57% and 62%, to light having a wavelength of 700 nm. In an embodiment, the zirconia sintered body includes yttrium oxide at a concentration of between 4.7 mol % and 5.3 mol %, such as between 4.9 mol % and 5.1 mol %.

In a fifth aspect, an unshaded zirconia sintered body includes a body containing yttria-stabilized zirconia having a flexural strength of at least 800 MPa, such as between 800 MPa and 900 MPa, and a total light transmittance value of at least 48%, such as between 48% and 52%, to light having a wavelength of 500 nm. In an embodiment, the zirconia sintered body includes yttrium oxide at a concentration of between 4.7 mol % and 5.3 mol %, such as between 4.9 mol % and 5.1 mol %.

In a sixth aspect, an unshaded zirconia sintered body includes a body containing yttria-stabilized zirconia having a flexural strength of at least 800 MPa, such as between 800 MPa and 1050 MPa, and a total light transmittance value of at least 46%, such as between 46% and 52%, to light having a wavelength of 500 nm. In an embodiment, the zirconia sintered body includes yttrium oxide at a concentration of between 4.0 mol % and 5.3 mol %, such as between 4.0 mol % and 5.1 mol %.

In a seventh aspect, a shaded zirconia sintered body includes a body containing yttria-stabilized zirconia having a flexural strength of at least 800 MPa, such as between 800 MPa and 900 MPa, and a total light transmittance value of at least 34%, such as between 34% and 40%, to light having a wavelength of 500 nm. In an embodiment, the zirconia sintered body includes yttrium oxide at a concentration of between 4.7 mol % and 5.3 mol %, such as between 4.7 mol % and 5.1 mol %.

In an eighth aspect, a shaded zirconia sintered body includes a body containing yttria-stabilized zirconia having a flexural strength of at least 800 MPa, such as between 800 MPa and 900 MPa, and a total light transmittance value of at least 52%, such as between 52% and 60%, to light having a wavelength of 700 nm. In an embodiment, the zirconia sintered body includes yttrium oxide at a concentration of between 4.7 mol % and 5.3 mol %, such as between 4.7 mol % and 5.1 mol %.

BRIEF DESCRIPTION OF THE FIGURE

FIG. 1 is a graphical representation of relative translucency difference ($\Delta T$) and CIE Value (L*) properties of shaded yttria-stabilized zirconia ceramic bodies.

DETAILED DESCRIPTION

Methods for making sintered ceramic bodies having high strength and translucency properties suitable for use as dental restorations, are provided. The methods preferably include a step of making a ceramic green body using a wet forming process (e.g., slip-casting, filter pressing, centrifugal casting), bisque heating the green body to form a ceramic bisqued body, and sintering the bisqued body (or parts formed from the bisqued body) to obtain a ceramic sintered body. The resulting ceramic sintered body has a combination of high strength and translucency desirable for forming dental restorations having high strength and esthetic properties comparable to those of natural teeth.

The following includes descriptions of high density green bodies and method for making high density green bodies; high density bisqued blocks and methods for making such bisqued blocks; and dental ceramic sintered bodies having a combination of high flexural strength and high translucency.

The present green body manufacturing method includes an improved slip-casting process that provides a green body having improved density when compared to conventional green body blocks. The green body formed by the improved slip-casting process is heated in a bisque-firing treatment to provide a bisqued block having improved properties such as density, porosity, and pore sizes when compared to conventional bisqued blocks. The green body manufacturing method includes the steps of providing starting materials; mixing and comminuting the starting materials to form a slip; and casting the slip into a desired green body form, such as a milling block. The bisqued body manufacturing method includes the additional step of bisque firing the green body block to obtain a bisqued block, wherein, in one embodiment, the relative density of the bisque block does not increase more than 3% beyond the green body density.

In the first step of the green body manufacturing method, the starting materials are provided. In a preferred embodiment, the starting materials include stabilized zirconia powder, a dispersant, and deionized water. Examples of stabilized zirconia powders suitable for use herein include yttria-stabilized zirconia that has been stabilized with approximately 0.1 mol % to approximately 8 mol % yttria, or approximately 2 mol % to approximately 4 mol % yttria, or from approximately 4 mol % to approximately 6 mol % yttria. Specific examples of yttria-stabilized zirconia powders include yttria-stabilized zirconia commercially available from Tosoh USA, such as Tosoh TZ-3YS (nominally containing 3 mol % yttria, or 3Y), Tosoh Zpex (nominally containing 4 mol % yttria, or 4 Y), and Tosoh Zpex® Smile (containing nominally 5-6 mol % yttria, such as 5.5 Y). In addition, mixtures of the foregoing examples (including mixtures that contain unstabilized zirconia, e.g., containing no yttria) are suitable for use herein in order to obtain a desired yttria concentration for a given zirconia powder starting material. For example, an yttria-stabilized zirconia powder having an yttria concentration of approximately 4.7 mol % is obtainable by mixing 1 part of a zirconia powder containing approximately 3 mol % yttria with 2.125 parts of a zirconia powder containing approximately 5.5 mol % yttria. Where actual yttria mol % in yttria-stabilized zirconia material may varying from nominal values, actual mol % yttria may be calculated, for example, based on compositional information received from manufacturer certification. In several preferred embodiments, the starting materials for forming a green body include yttria-stabilized zirconia powder having an yttria concentration of from approximately 4 mol % to 6 mol %, such as from approximately 4.5 mol % to approximately 5.5 mol %, such as from approximately 4.7 mol % to 5.3 mol %, and from approximately 4.7 mol % to 5.2 mol %.

The yttria-stabilized zirconia powders used as starting materials may optionally include a small amount of alumina (aluminum oxide, $Al_2O_3$) as an additive. For example, several of the examples described above include alumina at a concentration of from 0 wt % to 0.25 wt %, such as 0.1 wt %, relative to the zirconia powder. Other optional additives include coloring agents and esthetic additives, such as oxides, salts, or other compounds of erbium, terbium, chromium, cobalt, iron, manganese, nickel, praseodymium, and/or other coloring ions used to obtain shades in final sintered restorations that meet desired dental shaded, such as the 16 Vita® classical shades, and/or to obtain desired opalescence or fluorescence properties for dental applications. A coloring agent may comprise a metal selected from Tb, Er, Cr, or Co, and combinations thereof. Still other optional additives include alternative stabilizer materials, such as cerium oxide and/or magnesium oxide. Still other optional additives include grain growth inhibitors, sintering aids, and/or toughening aids.

The dispersants suitable for use in the slip-casting portion of the green body manufacturing method function by promoting the dispersion and stability of the slip and decreasing the viscosity of the slip. Dispersion and deflocculation occur through electrostatic, electrosteric, or steric stabilization. Examples of suitable dispersants include nitric acid, hydrochloric acid, citric acid, diammonium citrate, triammonium citrate, polycitrate, polyethyleneimine, polyacrylic acid, polymethacrylic acid, polymethacrylate, polyethylene glycols, polyvinyl alcohol, polyvinyl pyrillidone, carbonic acid, and various polymers and salts thereof. These materials may be either purchased commercially or prepared with well-known techniques. Specific examples of commercially available dispersants include Darvan® 821-A ammonium polyacrylate dispersing agent commercially available from Vanderbilt Minerals, LLC; Dolapix™ CE 64 organic dispersing agent and Dolapix™ PC 75 synthetic polyelectrolyte dispersing agent commercially available from Zschimmer & Schwarz GmbH; and Duramax™ D 3005 ceramic dispersant commercially available from Rohm & Haas Company.

The zirconia powder and dispersant starting materials are added to the deionized water to obtain a slurry. In the next method step, the slurry is subjected to a comminution process by which the zirconia powder particles are mixed, deagglomerated, and reduced in size. Comminution is performed using one or more milling processes, such as attritor milling, horizontal bead milling, ultrasonic milling, or other milling or comminution process, such as high shear mixing, ultra high shear mixing capable of reducing the zirconia powder particle sizes described herein. More particularly, the commercially available zirconia powder starting materials described above typically have a measured particle size $D_{(50)}$ of about 600 nm or more, which constitute agglomerations of particles of crystallites having an actual particle size of about 20-40 nm. As used herein, the term "measured particle size" refers to measurements obtained by a Brookhaven Instruments Corp. X-ray disk centrifuge analyzer. The comminution processes described herein are intended to reduce the measured particle size of the zirconia powder contained in the slurry from the $D_{(50)}$=600 nm range down to a range of from $D_{(50)}$=100-300 nm, such as from $D_{(50)}$=100-250 nm, or from $D_{(50)}$=150-250 nm, or from $D_{(50)}$=200-250 nm. The reduced particle size ranges of the zirconia powder component, in combination with the dispersants describe above, provide cast parts with a higher density and smaller pores, which in turn leads to sintered bodies having higher translucency and/or strength than those obtained by way of conventional pressing and slip-casting processes.

After the comminution step, the resulting slip is cast into a desired shape, such as a block, disk, near net shape, or other shape. In a preferred casting process, the comminuted slip is poured into a porous mold (e.g., plaster of paris or other porous/filtration media) having the desired shape, and cast, for example, under the force of capillary action, vacuum, pressure, or a combination thereof (See, e.g., US 2013/0313738, which is hereby incorporated by reference in its entirety). The zirconia particles contained in the slip will cast to form a green body in the desired shape as the water contained in the slip is absorbed/filtered through the porous media. Excess slip material, if any remaining, is poured off the green body and the green body is removed from the porous mold. Preferably, the green body is then allowed to dry at room temperature in a controlled, low humidity environment.

The preferred green body manufacturing processes described herein will provide green bodies having a relative density $\rho_R$ of greater than 56%, such as from 56-60%, or such as from 56-58%. As used herein, the term "relative density" ($\rho_R$) refers to the ratio of the measured density $\rho_M$ of a sample (g/cm$^3$) to the theoretical density of a sintered body $\rho_T$, where the theoretical density $\rho_T$ (g/cm$^3$) for a sintered zirconia body is assumed to be 6.0990 g/cm$^3$. I.e., $\rho_R=\rho_M/\rho_T$. As used herein, a ceramic body suitable for use in testing, such as flexural strength testing and translucency testing, is 'fully sintered', having a density that is about 98%, or greater, of the theoretical density of a sintered body.

The green body obtained from the slip-casting process is relatively fragile and not suitable for packaging, shipping, or machining processes. Accordingly, in the next step, the green body having the desired shape is subjected to a bisque firing step to obtain a bisqued body. The bisque firing step includes heating the green body at a temperature of from 900° C. to 1100° C. for a holding period of about 0.25 to 3 hours, or about 0.25 to 24 hours, or by other known bisquing techniques. Optionally, the difference between the relative densities of the bisque body and the green body is 3% or less. The resulting bisqued body is fully dried and has a strength sufficient to withstand packaging, shipping, and milling.

The preferred bisqued body manufacturing processes described herein will provide bisqued bodies having a relative density $\rho_R$ of greater than 57%, such as from 57% to 62%, such as from 58% to 62%, or such as from 59-62%. As used herein, the term "relative density" ($\rho_R$) refers to the ratio of the measured density $\rho_M$ of a sample (g/cm$^3$) to the theoretical density $\rho_T$, where the theoretical density $\rho_T$ (g/cm$^3$) of a sintered zirconia body is assumed to be 6.099 g/cm$^3$, (i.e., $\rho_R=\rho_M/\rho_T$.)

The preferred bisqued body manufacturing processes described herein will provide bisqued bodies also having a porosity of less than 43%, such as from 38% to 43%, or from 38% to 42%, or from 38% to 41%. As used herein, the term "porosity", expressed as percent porosity above, is calculated as: percent porosity=1−percent relative density. The pore size distributions are obtained from a bisqued body via mercury intrusion performed with an Autopore V porosimeter from Micromeritics Instrument Corp.

The preferred bisqued body manufacturing processes described herein will provide bisqued bodies also having a median pore diameter of from less than 90 nm, such as from 35-90 nm, or from 40-80 nm, or from 4070 nm, or from 40-60 nm. As used herein, the term "median pore diameter" refers to the pore diameter measurements obtained from a bisqued body via mercury intrusion performed with an Autopore V porosimeter from Micromeritics Instrument Corp.

The bisqued bodies described above, or parts made from the bisqued bodies, are used to make zirconia sintered bodies by undergoing a sintering process. In a preferred embodiment, a pre-sintered part is formed from a bisqued body using a material subtraction process, such as conventional milling or machining processes known to those skilled in the art, to form a pre-sintered shape. For dental applications, a pre-sintered shape may include a dental restoration such as a crown, a multi-unit bridge, an inlay or onlay, a veneer, a full or partial denture, or other dental restoration. In alternative embodiments, the bisqued body itself is used in the sintering process prior to machining.

In the sintering process, the bisqued body or part is sintered under atmospheric pressure at a sintering temperature of from 1200° C. to 1600° C., preferably from 1400° C. to 1580° C., more preferably from 1400° C. to 1450° C. The sintering hold time is preferably from about 0.25 hour to 48 hours, such as from 1 to about 4 hours, preferably from 1 to about 3 hours, more preferably from about 2 to about 2.5 hours.

White, unshaded zirconia sintered bodies obtained by the processes described herein demonstrate combinations of translucency (i.e., total light transmittance (NIST), or relative transmittance difference as described herein, at identified wavelengths) and flexural strength that have not been achieved by zirconia sintered bodies manufactured using previous conventional manufacturing methods. In particular, when an yttria-stabilized zirconia powder starting material is used that contains from 4.0 mol % to 5.3 mol % yttria, and more preferably from 4.0 mol % to 5.1 mol % yttria, the present methods provide zirconia sintered bodies having a flexural strength greater than 800 MPa, such as from 800-1050 MPa, while also providing a light transmittance value of at least 55%, or at least 56%, such as from 56% to 59%, for light having a wavelength of 700 nm or, alternatively, providing a light transmittance value of at least 46%, such as from 46% to 52%, for light having a wavelength of 500 nm. The relative translucency difference (ΔT) between the translucency of a sintered unshaded zirconia sintered body prepared according to the inventive methods described herein, and a 5.3 mol % yttria-stabilized standard, may be greater than −2, or from −2 to 1, at 700 nm, as determined according to the method herein.

Further, when an yttria-stabilized zirconia powder starting material is used that contains from 4.7 mol % to 5.3 mol % yttria, or from 4.7 mol % to 5.2 mol % yttria, or from 4.7 mol % to 5.1 mol % yttria, the present methods provide zirconia sintered bodies having a flexural strength greater than 800 MPa, such as from 800-900 MPa, while also providing a light transmittance value of at least 56%, or at least 57%, such as from 57% to 62%, such as from 58% to 62% for light having a wavelength of 700 nm or, alternatively, providing a light transmittance value of at least 48%, such as from 48% to 52%, for light having a wavelength of 500 nm. The relative translucency difference (ΔT) between the yttria-stabilized zirconia according to the invention and a 5.3 mol % yttria-stabilized standard, may be greater than −1, or (ΔT) is from −1 to 1, at 700 nm, according to the method described herein. In one embodiment, an yttria-stabilized ceramic material having from 4.7 mol % yttria to 5.3 mol % yttria, comprises a ΔT from −0.9 to 0.5.

In a further embodiment, yttria-stabilized zirconia ceramic material comprises between 4 mol % yttria and 5.1 mol % yttria, or between 4.5 mol % and 5.1 mol % yttria. The zirconia ceramic material may comprise a powder, a ceramic slurry, a green body, a bisque body or a sintered ceramic body. The material exhibits a flexural strength of at least 800 MPa and a total light transmittance of at least 55% at 700 nm, when shaped into a ceramic body and fully sintered. Zirconia ceramic material may comprise between 4.6 mol % yttria and 4.9 mol % yttria, or between 4.7 mol % and 5.1 mol % yttria, while having a total light transmittance of at least 56% at 700 nm, when fully sintered. A bisqued body made from this zirconia ceramic material may have a density between 57% and 62% of theoretical density and median pore diameter from 40 nm to 70 nm. In a further embodiment, the bisque body may comprise a particle size at D(50) that is from 100 nm to 300 nm. The yttria-stabilized zirconia ceramic material may further comprise a coloring agent comprising at least one metal selected from Tb, Cr, Er, and Co.

A zirconia ceramic material for use in dental applications may comprise an yttria-stabilized zirconia material comprising between 3.9 mol % yttria and 5 mol % yttria. The zirconia ceramic material may comprise a powder, a ceramic slurry, a green body, a bisque body or a sintered ceramic body. The zirconia ceramic material exhibits a strength of at least 800 MPa and ΔT from −2.5 to 0.5 at 700 nm, when shaped as a ceramic body and fully sintered. The zirconia ceramic material may comprise between 4.6 mol % yttria and 4.9 mol % yttria, and may have a ΔT that is from −1 to 0 at 700 nm when fully sintered. A coloring agent may be provided in the ceramic material that comprises at least one metal selected from comprising Tb, Cr, Er and Co. A bisqued body may be formed from the material having a density between 57% and 62% of theoretical density, a median pore diameter from 40 nm to 70 nm, and the particle size at D(50) may be from 100 nm to 300 nm.

Shaded zirconia sintered bodies obtained by the processes described herein also demonstrate combinations of translucency (i.e., total light transmittance at identified wavelengths) and flexural strength that have not been achieved by shaded zirconia sintered bodies manufactured using previous conventional manufacturing methods. In particular, when an yttria-stabilized zirconia powder starting material is used that contains from 4.0 mol % to 5.3 mol % yttria, and more preferably from 4.0 mol % to 5.1 mol % yttria, along with sufficient color/shade imparting elements to achieve a desired dental shade, such as a shade that is equivalent to a given Vita® Classical shade, the present methods provide shaded zirconia sintered bodies having a flexural strength of from greater than 800 MPa, such as from 800 to 1050 MPa, while also providing a total light transmittance value of at least 52%, such as from 52% to 60%, for light having a wavelength of 700 nm or, alternatively, providing a total light transmittance value of at least 34%, such as from 34% to 40%, for light having a wavelength of 500 nm, according to the method provided herein using NIST standard. The relative translucency difference (ΔT) between the shaded zirconia bodies made according to the methods herein and a 5.3 mol % yttria-stabilized standard (i.e., prepared according to CE2A, below) may be greater than −6, or from −6 to 2, at 700 nm (total light transmittance), as determined according to the method described herein.

Further, when an yttria-stabilized zirconia powder starting material is used that contains from 4.7 mol % to 5.3 mol % yttria, and more preferably from 4.7 mol % to 5.2 mol % yttria, along with sufficient color/shade imparting elements to achieve an equivalent to a given Vita® Classical shade, the present methods provide shaded zirconia sintered bodies having a flexural strength of from greater than 800 MPa, such as from 800-900 MPa, while also providing a light transmittance value of at least 52%, such as from 52% to 60% for light having a wavelength of 700 nm or, alternatively, providing a light transmittance value of at least 34%, such as from 34% to 40%, for light having a wavelength of 500 nm. The relative translucency difference (ΔT) between these materials and a 5.3 mol % yttria-stabilized standard may be greater than −6, or from −6 to 2, at 700 nm, as determined according to the method described herein.

Shaded, yttria-stabilized zirconia ceramic material comprising from 4.7 mol % to 5.1 mol % yttria, and optionally, alumina in an amount from 0 wt % to 0.25 wt %, exhibiting a flexural strength of at least 800 MPa, may comprise a coloring agent comprising at least one metal selected from Tb, Cr, Er, or Co. The shaded yttria-stabilized zirconia ceramic materials may further comprise from 4.7 mol % to 5.1 mol % yttria, or from 4.6 mol % to 4.9 mol % yttria. When shaped into a ceramic body and fully sintered, the ceramic bodies may exhibit a total light transmittance of at least 52%, or from 52% to 60%, at 700 nm. Relative Translucency Difference (ΔT) between shaded zirconia ceramic materials made by the slip-casting methods described herein and a pressed, unshaded 5.3 mol % yttria-stabilized zirconia may be greater than −6, or from −6 to 2 at 700 nm, when tested and measured by the method described herein.

Specific compositions of coloring agent may be used to achieve a desired dental shade that are visually equivalent throughout the Vita® Classical shades when examined by a trained dental restoration technician. For example, in one embodiment, to achieve a light shade (e.g., shade group 10, described herein) the coloring agent may comprise at least one metal selected from: Tb, measured as $Tb_4O_7$, in an amount from 0.005 wt % to 0.025 wt %; Cr, measured a $Cr_2O_3$, in an amount from 0.0002 wt % to 0.0009 wt %; Er, measured as $Er_2O_3$, in an amount from 0.022 wt % to 0.3 wt %; and Co, measured as $Co_3O_4$, in an amount from 0 wt % to 0.0001 wt %. The shaded zirconia ceramic material may exhibit a ΔT from to −3 to −1 at 700 nm when shaped into a ceramic body and fully sintered.

In a second embodiment, to achieve an intermediate shade (e.g., shade group 20) the coloring agent may comprise at least one metal selected from: Tb, measured as $Tb_4O_7$, in an amount from 0.01 wt % to 0.045 wt %, or from 0.015 wt % to 0.04 wt %; Cr, measured as $Cr_2O_3$, in an amount from 0.0005 wt % to 0.0015 wt %, or from 0.0006 wt % to 0.0017 wt %; Er, measured as $Er_2O_3$, in an amount from 0.015 wt % to 0.5 wt %, or from 0.016 wt % to 0.4 wt %; and Co, measured as $Co_3O_4$, in an amount from 0.00002 wt % to 0.0025 wt %. The shaded zirconia ceramic material may exhibit a ΔT from −4.5 to −3 at 700 nm, when fully sintered.

In a third embodiment, to achieve an intermediate darker shade (e.g., shade group 30), the coloring agent may comprise at least one metal selected from: Tb measured as $Tb_4O_7$ in an amount from 0.02 wt % to 0.06 wt %, or from 0.03 wt % to 0.06 wt %; Cr measured as $Cr_2O_3$ in an amount from 0.0007 wt % to 0.0025 wt %, or from 0.001 wt % to 0.0025 wt %; Er measured as $Er_2O_3$ in an amount from 0.02 wt % to 0.55 wt %, or from 0.02 wt % to 0.6 wt %; and Co measured as $Co_3O_4$ in an amount from 0.00008 wt % to 0.0045 wt %. The shaded zirconia ceramic material may exhibit a ΔT from −6 to −4 at 700 nm, when fully sintered.

In a fourth embodiment, to achieve a shade in the darkest shade group (e.g., shade group 40), the coloring agent may comprise at least one metal selected from: Tb, measured as $Tb_4O_7$, in an amount from 0.025 wt % to 0.08 wt %, or from 0.04 wt % to 0.08 wt %; Cr measured as $Cr_2O_3$ in an amount from 0.0009 wt % to 0.003 wt %, or from 0.0015 wt % to 0.003; Er measured as $Er_2O_3$ in an amount from 0.01 wt % to 0.6 wt %, or from 0.015 wt % to 0.6 wt %; and Co measured as $Co_3O_4$ in an amount from 0.0005 wt % to 0.006 wt %, or from 0.0017 wt % to 0.0055 wt %. The shaded zirconia ceramic material may exhibit a ΔT from −6 to −4 at 700 nm, when fully sintered.

Shaded zirconia material for use in dental applications comprising an yttria-stabilized zirconia material that comprises from 4.5 mol % yttria to 5.1 mol % yttria, or from 4.7 mol % to 5.1 mol % yttria, or from 4.6 mol % to 4.9 mol % yttria, and at least one coloring agent comprising a metal, may be shaped to form a ceramic body which, when fully sintered, exhibits a flexural strength greater 800 MPa and a CIE color space Value (L*) between 65 and 77. A plurality of shaded ceramic materials may be prepared by the disclosed methods that exhibit visual shade equivalence to a Vita® Classical shade when fully sintered. Each shade comprises an L* value, and a value for ΔT at 700 nm, (i.e., 5.3 mol % yttria-stabilized zirconia CE2A standard). A line graphed from plotted points (L* and ΔT at 700 nm) of multiple shades comprises good fit yielding an equation (i.e., 0.632 (L*)−49.164), as illustrated in FIG. 1. For a given L*, ΔT of a shaded zirconia materials may be calculated according to the equation 0.632 (L*)−49.164, plus or minus, for example, (+) 1.5. In an embodiment, shaded ceramic materials having an L* value between 65 and 77, have ΔT at 700 nm in the range of 0.632 (L*)−49.164)+1, or a ΔT value that is in the range of (0.632 (L*)−49.164)±0.75. The shaded ceramic materials may comprise at least one metal selected from Tb, measured as $Tb_4O_7$, in an amount from 0 wt % to 0.066 wt %; Cr, measured as $Cr_2O_3$, in an amount from 0 wt % to 0.0025 wt %; Er, measured as $Er_2O_3$, in an amount from 0 wt % to 0.78 wt %; and Co, measured as $Co_3O_4$, in an amount from 0 wt % to 0.007 wt %.

In a further embodiment, a shaded zirconia ceramic material comprising an yttria-stabilized zirconia having from 4.5 mol % yttria to 5.1 mol % yttria, or from 4.7 mol % yttria to 5.1 mol % yttria, and at least one coloring agent comprising a metal selected from terbium (Tb), chromium (Cr), erbium (Er) or Cobalt (Co). ΔT from −6 to 2 at 700 nm, is calculated as the difference between the percent translucency of the shaded zirconia ceramic material of the invention and an unshaded 5.3 mol % yttria-stabilized zirconia (i.e., CE2A). A CIE Value (L*) between 65 and 77, and a flexural strength greater than 800 MPa, may be achieved when shaped as a ceramic body and fully sintered. In other embodiments, shaded zirconia ceramic material may have an L* value between 73.5 and 76.5, and ΔT from −4 to 0; or an L* value between 71 and 74, and ΔT from −6 to −1; or L* value between 68 and 72.5 and ΔT from −2 to −6; or L* value between 66 and 71 and ΔT from −6 to −3.

In a further embodiment, a shaded sintered zirconia material having yttria-stabilized zirconia having from 4.6 mol % yttria to 4.9 mol % yttria, and at least one coloring agent comprising a metal selected from Tb, Cr, Er or Co, exhibits a flexural strength of greater than 800 MPa, and an L* value between 73 and 76, and a ΔT between −1 and −3, when shaped as a ceramic body and fully sintered. In alternate embodiments, the shaded ceramic material has an L* value between 71 and 73.5, and ΔT from −2 to −5; or an L* value between 69 and 71 and ΔT between −4 and −6; or an L* value between 66 and 70, and ΔT from −6 to −5.

Test Methods

Density

For the examples described herein, density calculations of ceramic bodies were determined as follows. The density of green body blocks were calculated by measuring the weight and dividing by the volume calculated from the dimensions of the green block. The density of bisqued body blocks were determined by liquid displacement methods of Archimedes principle. Flat wafers were sectioned from a bisqued block and dried prior to measuring the dry mass. Samples were then saturated with deionized water under vacuum (29-30 in Hg vacuum pressure) for one hour prior to measuring the suspended and saturated masses. All masses were measured to four decimal points precision. A theoretical density of 6.0990 g/mL was assumed for purposes of calculating relative density of the green body and bisqued body zirconia samples. For purposes herein, a ceramic material that is fully sintered has a density that is about 98%, or greater, of the theoretical density.

Flexural Strength

Samples for three-point bend strength (flexural strength) testing were milled and prepared according to ISO 6872: 2015 for the preparation of strength testing for dental ceramic materials. Results are provided in MPa. Flexural strength bars of ceramic materials were milled out of a bisqued block then ground flat with 1200 grit SiC polishing paper until visually free of defects. The bisqued bars were ground to a thickness corresponding to approximately 1.68× 25×4 mm3 after sintering. After sintering, the central region of both the tensile and compressive surfaces were visually inspected for defects by optical microscope. The side with the fewest observed defects was chosen as the side broken in tension (face-down in the test fixture). Flexural testing was performed on a Shimadzu EZ-Test universal testing machine with a custom built three-point bend fixture according to ISO 6872. The bars were aligned on the two rollers using a metal guide. Sample sets contained at least 10 bars. Flexural strengths were calculated via the measured breaking load and measured dimensions.

Translucency

Sintered body translucency was determined by measuring the percent transmittance of D65 light at a wavelength of 700 nm from a 1 to 1.1 mm thick sintered sample. Translucency wafers were sectioned from a bisqued block and machined to a diameter corresponding to a final diameter of approximately 30 mm after sinter. The wafers were then ground flat until visually free of defects with 1200 and 2000 grit SiC polishing paper. The final bisqued thickness corresponded to 1.0 mm after sintering. Samples ground to the desired shape were removed of surface dust and then sintered according to the sintering profile(s) described herein.

After sintering, samples were cleaned with isopropanol to remove errant surface material; however, no further surface preparation techniques were applied to the samples prior to testing. Total transmittance spectra were measured between the wavelengths of 360 to 740 nm with a Konica-Minolta CM5 spectrophotometer illuminated by a D65 light source for all samples along with the CE2A comparison standard. Information contained in the data tables herein refer to measurements at 700 nm wavelength, which are extracted from these measurements. The spectrophotometer was calibrated to white and black prior to measurement. Translucency samples were placed flush against the (approximately) 25 mm integrating sphere aperture. A minimum of two spectra were collected per sample and averaged to yield a final measured transmittance spectra (S-TM).

Collected transmittance data may be reported as "percent (%) transmittance (raw)". Collected transmittance data may be corrected and reported as percent (%) transmittance NIST, based on NIST corrected data, as described below. Collected data may be compared to a standard to calculate relative translucency difference, reported as $\Delta T$, as described below.

1) NIST Correction Method for Obtaining Percent Transmittance:

Measured transmittance spectra was obtained and corrected for instrumental variation using a NIST traceable neutral density filter (optical density of 0.3, Avian Technologies TF-ND03-02c) to obtain the transmittance spectra S-TA. The NIST traceable neutral density filter was measured between the wavelengths of 360 to 740 nm with the Konica-Minolta CM5 spectrophotometer illuminated by a D65 light source and compared to the provided certificate of analysis spectrum, N-TA. The difference between the actual spectra, N-TA, and the measured spectrum, N-TM, was averaged over the entire wavelength range to determine the instrumental variation in transmittance, IV. This instrumental variation (IV) was subtracted from the measured spectra for the sample (S-TM) to obtain the corrected transmittance S-TA for the samples. The corrected transmittance spectra (S-TA) at a wavelength of e.g., 700 nm or 500 nm, is reported in the data tables contained herein as "percent (%) transmittance (NIST)".

2) Relative Translucency Difference ($\Delta T$) Between Sample and Standard:

To provide consistency between calibration runs and to account for variability between equipment, the samples were measured and calculated for relative translucency difference with an unshaded, 5.3 mol % yttria-stabilized zirconia standard. For purposes herein, Relative Translucency Difference ($\Delta T$) is calculated as the difference between the measured percent transmittance of a standard material and the measured percent transmittance of a sample. Where indicated for data reported herein, relative translucency differences of samples are obtained by comparison to example CE2A.

The standard (Example CE2A) was prepared from commercially available 5.3 mol % yttria-stabilized zirconia material (Zpex Smile, nominally 5.5 Y, Tosoh USA), $ZrO_2$, $HfO_2$, $Y_2O_3$, and $Al_2O_3$ having a combined weight percent of greater than 99.9% of the yttria-stabilized zirconia composition, and wherein the weight percentages of $Y_2O_3$ is 9.35+0.2%, $Al_2O_3$ is 0.05+0.01%, $SiO_2$ is <0.02%, and $Fe_2O_3$ is <0.01%.

Unshaded, 5.3 mol % yttria-stabilize zirconia powder was pressed into a 98 mm×15 mm disc block in a uniaxial press at pressure sufficient to obtain a green block having a density of 3.21+/−0.02 g/cm$^3$. The pressed body was bisque fired as follows: RA1: 30° C./hr to 130° C., hold time 0 hours; RAZ 9° C./hr to 180° C., hold time 4 hours; RA3: 6° C./hr to 210° C., hold 4 hours; RA4: 3° C./hr to 250° C., hold 9 hours; RA5: 9° C./hr to 350° C., hold 4 hours; RA6: 420° C./hr to 400° C., hold time 0 hours; RA7: 120° C./hr to 1050° C., hold 2 hours; RA8: 120° C./hr to 20° C., hold 0 hours. The bisqued body was milled into wafers and prepared as above.

The bisqued body wafers as described above were sintered as follows. Step 1—oven was raised from room temperature to 1200° C. at a programmed rate of 15° C./min. and held at 1200° C. for 1 hour; Step 2—the oven temperature was raised from 1200° C. to 1300° C. at a programmed rate of 2° C./min.; Step 3— the oven temperature was raised from 1300° C. to 1530° C. at a programmed rate 10° C./min. and held at 1530° C. for 150 minutes; Step 4—the oven was cooled at a rate of about 15° C./min or slower prior to removing the samples.

Total transmittance spectra were measured between the wavelengths of 360 to 740 nm with a Konica-Minolta CM5 spectrophotometer illuminated by a D65 light source for all samples as well as the CE2A comparison standard. Relative translucency difference ($\Delta T$) between the exemplary ceramic bodies and the CE2A standard, were based on measurements obtained at 700 nm, calculated as follows:

$$\Delta T = \% \, T@700 \text{ nm Sample} - \% \, T@700 \text{ nm CE2A}$$

Color Space (CIE L*a*b) Test

Zirconia materials were measured for color space according to CIE L*a*b* (International Commission on Illumination, measuring two polar axes for color, 'a*' and 'b*', and value (lightness, L*)) values using a Konica Minolta Spectrometer with a D65 light source.

27 mm diameter sintered test wafers were cut from bisque blocks. The final thickness of the test wafers after sintering was 1.0 mm. Therefore, the starting thickness for each wafer was calculated based on the targeted final thickness taking into consideration the enlargement factor (EF) as follows:

$$\text{Final thickness} \times (EF) = \text{bisque wafer thickness.}$$

To measure color, the Konica Minolta CM5 Spectrometer was set on reflectance mode using the Specular Component Included (SCI) mode, with a D65 light source, and 11 mm target mask (aperture diameter). The L*a*b* values were measured with the samples placed flush and centered against the aperture with no backing material to back-reflect light. These values were referenced to materials made from traditional processes.

Mercury Porosimetry

Pore size distributions were measured on 1-4 gram samples obtained from a bisqued block. Samples were dried before mercury intrusion. Intrusion was performed with a Micromeritics Autopore V porosimeter with set pressure ranges from total vacuum to 60,000 psi using Micromeritics penetrometers models #07 and #09. The median pore diameter (volume) from the measurement was reported as the Median pore diameter.

Particle Size Distribution

Particle size distributions were measured with a Brookhaven Instruments Corp. X-ray disk centrifuge analyzer. Samples were collected from the source suspension and kept agitated until measurement.

EXAMPLES

Green Body and Bisqued Body Manufacturing Using Slip Casting

Green body and bisqued body samples were prepared using a slip casting method and using two commercially available yttria-stabilized zirconia powders nominally referred to by the manufacturer (Tosoh USA) as 3Y and 5.5Y. According to product sheets provided by the manufacturer, 3Y contains approximately 2.9 mol % yttria, rather than 3 mol %, and 5.5Y contains approximately 5.3 mol % yttria, rather than 5.5 mol %, as indicated in Tables 1A, 2a-c, 4 and 5, below. The two zirconia powders were blended to provide a range of yttria content in the yttria-stabilized zirconia ceramic powders and bodies. Nominal yttria content calculated from nominal values, are reported as #Y, such as 4.9Y. Actual mol % yttria content for blends are calculated from the mol % yttria provided with the product sheet, and reported as (actual) mol % yttria, as in Table 1A.

For each example, the yttria-stabilized zirconia powders and the dispersant (Dolapix CE 64) were added to deionized water to form a slurry having a solids concentration of from about 69-80% solids to create a material with the desired actual yttria composition.

In the case of the slip-cast examples of shaded zirconia containing coloring compounds, appropriate coloring compounds were added to obtain equivalent Vita® Classical Shades and a bleach shade, as described in Table 1B (all percentages based on percentage by weight as a percentage of zirconia). Colorants were calculated on an oxide basis and were added as hydrated salts and oxide powders pre-reacted with zirconia. For colorants that have relatively higher concentrations of colorants (e.g., erbium oxide and terbium oxide), they were added in solid form to the slip as oxides pre-reacted with zirconia. For colorants with low concentrations (e.g., chromium oxide and cobalt oxide), they were added as a salt to the slip.

The slurry was mixed for approximately 5 minutes using a high-shear mixer, then added to the mixing tank of a horizontal bead mill. Horizontal bead milling was performed on the slurry at a rate of from about 6 to about 16 kg dry mass per hour to obtain a slip for slip casting. The mixing and milling steps also allow for complete homogenization of the colorant into the zirconia slip for shaded Examples. After milling, the slurry was drained from the horizontal bead mill and passed through a 20 $\rho_M$ sieve to remove milling media and other contamination.

TABLE 1A

Bisqued Ceramic Bodies Prepared By Slip-Casting Process

| Example No. | Nominal Yttria composition | Actual Yttria Composition (mol %) | Coloring compounds | Example Shade |
|---|---|---|---|---|
| 1 | 4Y | 3.9 mol % | None | Unshaded (white) |
| 2 | 4.7Y | 4.6 mol % | None | Unshaded (white) |
| 3 | 4.9Y | 4.7 mol % | None | Unshaded (white) |
| 4 | 5.1Y | 4.9 mol % | None | Unshaded (white) |
| 5 | 5.2Y | 5.0 mol % | None | Unshaded (white) |
| 6 | 4.9Y B1 | 4.7 mol % | $Er_2O_3$, $Tb_4O_7$, $Cr_2O_3$, $Co_3O_4$ | B1 |
| 7 | 4.9Y A3.5 | 4.7 mol % | $Er_2O_3$, $Tb_4O_7$, $Cr_2O_3$, $Co_3O_4$ | A3.5 |
| 8 | 4.9Y C2 | 4.7 mol % | $Er_2O_3$, $Tb_4O_7$, $Cr_2O_3$, $Co_3O_4$ | C2 |

TABLE 1B

Colorant Concentrations (Weight percent) In an Yttria-Stabilized Zirconia Material To Obtain Equivalent Vita ® Classical Shades

| Shade Group/Equivalent Vita ® Classical Shade(s) | | $Er_2O_3$ | $Tb_4O_7$ | $Cr_2O_3$ | $Co_3O_4$ |
|---|---|---|---|---|---|
| Equivalent 16 Vita ® Classical Shades | | 0-0.78 wt % | 0-0.066 wt % | 0-0.0025 wt % | 0-0.007 wt % |
| Equivalent B1 Vita ® Classical Shade | | 0.052-0.079 wt % | 0.0063-0.0095 wt % | 0.0002-0.0004 wt % | 0.0009-0.0013 wt % |
| Equivalent A3.5 Vita ® Classical Shade | | 0.3-0.45 wt % | 0.03-0.046 wt % | 0.001-0.002 wt % | 0.0015-0.0023 wt % |
| Shade Group 10 | Bleach, A1, A2, B1, B2 | 0.02-0.3 wt % | 0.005-0.025 wt % | 0.0002-0.0009 wt % | 0-0.001 wt % |
| Shade Group 20 | A3, A3, B3, B4, C1, C2, D2 | 0.016-0.4 wt % | 0.015-0.04 wt % | 0.0006-0.0017 wt % | 0.00002-0.0025 wt % |
| Shade Group 30 | A3.5, C3, D3, D4 | 0.02-0.55 wt % | 0.03-0.06 wt % | 0.001-0.0025 wt % | 0.00008-0.0045 wt % |

TABLE 1B-continued

Colorant Concentrations (Weight percent) In an Yttria-Stabilized Zirconia Material To Obtain Equivalent Vita ® Classical Shades

| Shade Group/Equivalent Vita ® Classical Shade(s) | | $Er_2O_3$ | $Tb_4O_7$ | $Cr_2O_3$ | $Co_3O_4$ |
|---|---|---|---|---|---|
| Shade Group 40 | A4, C4 | 0.15-0.6 wt % | 0.04-0.08 wt % | 0.0015-0.003 wt % | 0.0017-0.0055 wt % |

The slip obtained from the horizontal bead mill was cast into molds to form cast blocks. Two sizes of molds were used to form disk shaped blocks having a first size of 98 mm diameter×15 mm thickness, and a second size of 33 mm diameter×20 mm thickness. After casting, the blocks were placed in a dryer at ambient temperature and weighed at 12 hour increments until the weight of the block had stabilized. Dry green body blocks were loaded into a bisquing oven where the blocks were bisque fired at a final hold temperature of 950° C. for a hold time of 2 hours to form bisqued body blocks.

Green Body and Bisqued Body Manufacturing Using Press Manufacturing

Green body and bisqued body samples were prepared using a uniaxial press manufacturing method for comparative purposes.

The starting materials were two commercially available yttria-stabilized zirconia powders referred to by the manufacturer (Tosoh USA) as Zpex® 4 and Zpex® Smile (nominally available as 4Y and 5.5Y), respectively, as described in Table 2A. According to product data sheets obtained from the manufacturer, yttria content of the zirconia starting materials may be within the following ranges: Zpex® 4Y yttria content is 3.89 mol % (hereinafter, 3.9 mol %), and Zpex® Smile 5.5Y yttria content is from 5.21 mol % to 5.45 mol % (5.3 mol %). For purposes herein, in Tables 1A, 2a-2c, and 4-5, actual yttria concentrations are reported as mol %, and nominal values are reported as #Y.

For shaded, pressed, zirconia bodies having a visually equivalent shade as the listed Vita® Classical shades B1 and A3.5, colorants consisted of pre-reacted compounds of zirconia as commercially available from Tosoh USA and outlined in Tables 2B and Table 2C. These pre-reacted (pre-colored) zirconia powders (pink, yellow and gray) were added to unshaded, white, yttria-stabilized zirconia powder (e.g., Zpex® 4 (4Y) and Zpex® Smile (5.5Y), Tosoh USA) in dry form and suitably dry-mixed to obtain homogeneity prior to uniaxial pressing.

The zirconia powders were pressed into 98 mm×15 mm blocks in a uniaxial press at pressure sufficient to obtain green blocks having a density of 3.21±0.02 g/cm³. Blocks were removed from the press and subjected to a bisque firing with a slow initial ramp rate to 350° C. to remove the binder, and then held for 2 hours at a final hold temperature of 1050° C. to obtain bisqued body blocks.

TABLE 2A

Press Manufactured Bisqued Body Samples - Comparative Examples

| Example No. | Nominal Yttria Composition | Actual mol % Yttria Composition | Coloring compounds | Sample shade |
|---|---|---|---|---|
| CE1 | 4Y | 3.9 mol % | None | Unshaded (white) |
| CE2 | 5.5Y | 5.3 mol % | None | Unshaded (white) |
| CE3 | 4Y | 3.9 mol % | Zpex ® pink, Zpex ® 4 yellow, Zpex ® Smile gray | B1 |
| CE4 | 5.5Y | 5.3 mol % | Zpex ® pink, Zpex ® Smile yellow, Zpex ® Smile gray | B1 |
| CE5 | 4Y | 3.9 mol % | Zpex ® pink, Zpex ® 4 yellow, Zpex ® Smile gray | A3.5 |
| CE6 | 5.5Y | 5.3 mol % | Zpex ® pink, Zpex ® Smile yellow, Zpex ® Smile Gray gray | A3.5 |

TABLE 2B

Colorant Blends for Pressed Bisqued Body Samples (4Y)

| Ex. No. | Actual mol % yttria (Nominal yttria) | Vita ® Shade | Zpex ® 4 unshaded (4Y) | Zpex ® 4 Yellow (4Y) | Zpex ® Pink (3Y) | Zpex ® Smile Gray (5.5Y) | Total (%) |
|---|---|---|---|---|---|---|---|
| CE3 | 3.9 mol % (4Y) | B1 | 67 | 27.8 | 1.2 | 4 | 100 |
| CE5 | 3.9 mol % (4Y) | A3.5 | 21.44 | 64.8 | 7.15 | 6.61 | 100 |

TABLE 2C

Colorant Blends for Pressed Bisqued Body Samples (5.5Y)

| Ex. No. | Actual mol % yttria (Nominal yttria) | Vita ® Shade Equivalent | Zpex ® Smile unshaded (5.5Y) | Zpex ® Smile Yellow (5.5Y) | Zpex ® Pink (3Y) | Zpex ® Smile Gray (5.5) | Total (%) |
|---|---|---|---|---|---|---|---|
| CE4 | 5.3 mol % (5.5Y) | B1 | 83.4 | 13 | 0.7 | 2.9 | 100 |
| CE6 | 5.3 mol % (5.5Y) | A3.5 | 53.2 | 36.5 | 5.3 | 5 | 100 |

Sintering

Zirconia sintered bodies were prepared from the bisqued blocks described above. Sample zirconia wafers were milled from the prepared bisqued blocks and were sintered for 2.5 hours at temperatures listed in Tables 4 and 6.

Testing and Results

Samples obtained from the green blocks were tested for density according to the testing methods described above. Samples obtained from the bisqued blocks were tested for density, porosity, and median pore diameter according to the testing methods described above. In addition, enlargement factors (EF=inverse cubic root of the bisqued block relative density) were calculated based upon the measured densities. The results of the testing are shown below in Table 3.

TABLE 3

Green Body and Bisqued Body Testing and Results

| Example No. | Green Body Relative Density (%) | Bisqued Block Relative Density (%) | Bisqued Block EF (Calc) | Bisqued Block Porosity (%) | Bisqued Block Median Pore Diameter (nm) |
|---|---|---|---|---|---|
| 1 | 57.5 | 59.5 | 1.189 | 40.5 | — |
| 2 | 57.3 | 59.2 | 1.191 | 40.8 | 60 |
| 3 | 57.3 | 59.7 | 1.187 | 40.3 | 57 |
| 4 | 58.0 | 59.7 | 1.188 | 40.4 | 58 |
| 5 | 57.9 | 59.7 | 1.187 | 40.3 | 57 |
| CE1 | 52.6 | 53.2 | 1.234 | 46.8 | 59 |
| CE2 | 52.7 | 53.2 | 1.234 | 46.8 | 81 |

The testing showed that the relative densities of the green bodies and bisqued bodies prepared according to the slip casting methods described herein were significantly higher than the densities of the green bodies and bisqued bodies prepared by conventional press manufacturing. Similarly, the porosity values and median pore diameters for the bisqued bodies manufactured using the slip casting methods were significantly lower than the corresponding properties of the bisqued bodies prepared by press manufacturing. The change in relative density from green body to bisque body was less than 3%.

Sintered body samples were tested for flexural strength and translucency according to the testing methods described above. The results of the strength and translucency testing are shown below for unshaded examples, in Table 4. Total translucency values calculated using the NIST correction method for obtaining percent translucency for values are reported at 700 nm and 500 nm. Relative Translucency Difference ($\Delta T$) values were calculated from total light transmittance at 700 nm according to the method described herein for determining $\Delta T$ between the Examples and CE2A (unshaded 5.3 mol % yttria-stabilized zirconia, pressed and sintered at 1530) C. ° as a standard.

TABLE 4

White (Unshaded) Sintered Body Translucency (NIST) and Strength Results

| Example No. | Actual mol % Yttria (Nominal Y Comp.) | Sintering Temp (° C.) | Flexural Strength (MPa) | Total Light Transmittance % at 700 nm: NIST corrected/(raw) | $\Delta T$ at 700 nm compared to CE2A | Total Light Transmittance % at 500 nm (NIST) |
|---|---|---|---|---|---|---|
| 1A | 3.9 mol % (4.0) | 1450 | 995 | 56.4/(56.7) | −1.7 | 46.4 |
| 1B | 3.9 mol % (4.0) | 1550 | 1060 | 55.7/(56.0) | −2.4 | |
| 2A | 4.6 mol % (4.7) | 1450 | 890 | 57.2/(57.5) | −0.9 | 48.1 |
| 2B | 4.6 mol % (4.7) | 1530 | 861 | 58.0/(58.3) | −0.1 | |
| 3 | 4.7 mol % (4.9) | 1450 | 870 | 57.4/(57.7) | −0.7 | 48.4 |
| 4 | 4.9 mol % (5.1) | 1450 | 803 | 57.9/(58.2) | −0.2 | 49.0 |
| 5 | 5.0 mol % (5.2) | 1425 | 817 | 58.6/(58.9) | 0.5 | |
| CE1 | 3.9 mol % (4Y) | 1550 | 1021 | 54.7/(55.0) | −3.4 | 46.0 |
| CE2A (standard) | 5.3 mol % (5.5Y) | 1530 | 650 | 58.1/(58.4) | NA | 49.0 |
| CE2B | 5.3 mol % (5.5Y) | 1450 | 762 | 56.5/(56.8) | −1.6 | 47.7 |

Shaded sintered body samples were also tested for flexural strength and translucency (total light transmittance at 700 nm and 500 nm calculated with NIST correction method and relative translucency difference) according to the test methods described above. The results of the testing are shown below in Table 5.

In FIG. 1, for Examples 9 through 25, the Relative Translucency Difference ($\Delta T$) between each example and CE2A is plotted against the CIE Value ($L^*$) for each example, providing the linear equation $\Delta T=0.632(L^*)-49.164$, where coefficient correlation squared ($R^2$) is 0.969.

TABLE 5

Shaded Sintered Body Testing and Results

| Ex. No. | Actual mol % Yttria (Nominal Y comp.) | Sintering Temp (° C.) | Equiv. Vita ® Class. Shade | Flexural Strength (MPa) | Total Light Trans. % at 700 nm (NIST) | ΔT at 700 nm compared to to CE2A | Total Light Transmittance % at 500 nm (NIST) |
|---|---|---|---|---|---|---|---|
| 6   | 4.7 mol % (4.9Y) | 1450 | B1   | 852 | 56.9 | −1.2  | 38.1 |
| 7   | 4.7 mol % (4.9Y) | 1450 | A3.5 | 874 | 53.7 | −4.4  | 32.3 |
| 8   | 4.7 mol % (4.9Y) | 1450 | C2   | 921 | 53.4 | −4.7  | 35.4 |
| CE3 | 3.9 mol % (4Y)   | 1550 | B1   | 993 | 50.9 | −7.2  | 32.6 |
| CE4 | 5.3 mol % (5.5Y) | 1530 | B1   | 598 | 58.6 | 0.5   | 43.4 |
| CE5 | 3.9 mol % (4Y)   | 1550 | A3.5 | 959 | 46.4 | −11.7 | 19.5 |
| CE6 | 5.3 mol % (5.5Y) | 1530 | A3.5 | 621 | 56.3 | −1.8  | 32.8 |

The test results showed that sintered bodies obtained from the bisqued bodies, both shaded and unshaded, produced using the slip casting methods described herein provide a combination of higher flexural strength and higher percent translucency, or lower $\Delta T$ values (measured as total light transmittance value to light having wavelengths of 500 nm and 700 nm) than comparable sintered bodies obtained from press manufactured blocks.

For Examples 9 to 25, shaded ceramic bodies comprising approximately 4.7 mol % yttria-stabilized zirconia ceramic bodies were prepared by a slip-casting technique substantially according to the method provided for Examples 1-8. Colorant concentrations are provided for Shade Groups 10, 20, 30 and 40, in Table 1B. Samples prepared for each shade group 10-40 (Group 10: light to Group 40: dark) had color equivalence to Vita® Classical shades as determined by a trained technician, as seen in Table 6. CIE ($L^*a^*b^*$) color space was measured according to the methods provided herein. Relative translucency difference ($\Delta T$) was measured against CE2A, unshaded 5.3 mol % yttria-stabilized zirconia, as described in the methods provided herein. Results are reported in Table 6.

TABLE 6

Color Space And Translucency of Shaded Yttria-Stabilized Zirconia Ceramic Bodies.

| Example No. | Shade Group | Equivalent VITA ® Classical Shades | L* | a* | b* | ΔT at 700 nm |
|---|---|---|---|---|---|---|
| 9  | Shade Group 10 | bleach | 75.13 | −1.77 | 3.69   | −1.8 |
| 10 |                | A1     | 73.76 | −1.24 | 8.08   | −2.6 |
| 11 |                | B1     | 74.52 | −2.18 | 6.20   | −1.8 |
| 12 |                | B2     | 73.78 | −1.87 | 8.52   | −2.2 |
| 13 | Shade Group 20 | A2     | 72.91 | −0.80 | 10.40  | −2.8 |
| 14 |                | A3     | 72.59 | −0.57 | 10.95  | −3.3 |
| 15 |                | B3     | 71.62 | −0.64 | 13.88  | −4.2 |
| 16 |                | B4     | 71.54 | −0.51 | 14.41  | −4.5 |
| 17 |                | C1     | 72.75 | −1.99 | 7.68   | −3.2 |
| 18 |                | C2     | 72.02 | −1.47 | 9.88   | −3.8 |
| 19 |                | D2     | 72.29 | −1.12 | 8.15   | −3.5 |
| 20 | Shade Group 30 | A3.5   | 70.3  | 0.26  | 15.875 | −4.8 |
| 21 |                | C3     | 69.33 | −0.75 | 12.23  | −5.2 |
| 22 |                | D3     | 70.36 | −0.28 | 11.89  | −4.6 |
| 23 |                | D4     | 69.91 | −1.29 | 14.20  | −5.0 |
| 24 | Shade Group    | A4     | 69.05 | 0.67  | 14.62  | −5.7 |
| 25 |                | C4     | 67.01 | −0.04 | 14.10  | −6.4 |

The $\Delta T$ for a given example is within approximately +/−0.5 of $0.632(L^*)-49.164$.

We claim:

1. A bisque state zirconia ceramic material for use in dental applications comprising:
   an yttria-stabilized zirconia material comprising between 4 mol % yttria and 5.1 mol % yttria, having a relative density between 57% and 62% and median pore diameter from 40 nm to 70 nm.

2. The bisque state zirconia ceramic material of claim 1, wherein the yttria-stabilized zirconia material comprises between 4.5 mol % yttria and 5.1 mol % yttria.

3. The bisque state zirconia ceramic material of claim 1, wherein the yttria-stabilized zirconia material comprises between 4.6 mol % yttria and 5.1 mol % yttria.

4. The bisque state zirconia ceramic material of claim 1, wherein the zirconia ceramic material is in the form of a bisque block having an enlargement factor (EF) of less than 1.2.

5. The bisque state zirconia ceramic material of claim 1, wherein the zirconia ceramic material is in the form of a bisque body that comprises a particle size at D(50) that is from 100 nm to 300 nm.

6. The bisque state zirconia ceramic material of claim 1, wherein the zirconia ceramic material is in the form of a bisque body that comprises a porosity of less than 43%.

7. The bisque state zirconia ceramic material of claim 1, wherein the zirconia ceramic material is in the form of a bisque body that comprises a porosity of 38% to 43%.

8. The bisque state zirconia ceramic material of claim 1, wherein the zirconia ceramic material is in the form of a bisque body that comprises a porosity of 38% to 42%.

9. The bisque state zirconia ceramic material of claim 1, wherein the zirconia ceramic material is in the form of a bisque body that comprises a porosity of 38% to 41%.

* * * * *